United States Patent [19]

Reinhold

[11] 4,097,490
[45] Jun. 27, 1978

[54] PYROGLUTAMIC ACID SALTS OF t-BUTYLAMINO-2,3-DIHYDROXYPROPANE

[75] Inventor: Donald F. Reinhold, North Plainfield, N.J.

[73] Assignee: Merck & Co., Inc., Rahway, N.J.

[21] Appl. No.: 767,183

[22] Filed: Feb. 9, 1977

Related U.S. Application Data

[63] Continuation of Ser. No. 615,941, Sep. 25, 1975, abandoned, which is a continuation-in-part of Ser. No. 532,547, Dec. 13, 1974, abandoned.

[51] Int. Cl.$^2$ ............................................. C07D 207/28
[52] U.S. Cl. ............................... 260/326.45; 260/536; 424/274
[58] Field of Search ...................... 260/326.45, DIG. 8

[56] References Cited

U.S. PATENT DOCUMENTS

| 2,528,267 | 10/1950 | Dearborn et al. | 260/326.45 |
| 2,767,213 | 10/1956 | Long | 260/DIG. 8 |
| 3,116,332 | 12/1963 | Sullivan | 260/584 |
| 3,255,190 | 6/1966 | Broh-Kahn | 260/326.45 |
| 3,657,237 | 4/1972 | Weinstock et al. | 260/247.1 |
| 3,862,132 | 1/1975 | Irda et al. | 260/DIG. 8 |
| 3,940,406 | 2/1976 | Raabe et al. | 260/296 AE |

FOREIGN PATENT DOCUMENTS

| 2,185,411 | 5/1972 | France | 260/290 AE |
| 1,243,206 | 6/1967 | Germany | 260/584 |
| 38-17678 | 1963 | Japan | 260/326.45 |
| 773,648 | 5/1957 | United Kingdom | 260/DIG. 8 |

OTHER PUBLICATIONS

Morrison et al.; Organic Chemistry, 3rd Ed., pp. 236–237 (1974).
Iliceto; Chem. Abs. vol. 49; pp. 929–930 (1955).

Primary Examiner—Donald G. Daus
Assistant Examiner—Mary Vaughn
Attorney, Agent, or Firm—Daniel T. Szura

[57] ABSTRACT

Process for resolving enantiomers of 1-t-butylamino-2,3-dihydroxypropane using a pyroglutamic acid or a tartaric acid as resolving agent. The enantiomers of 1-t-butylamino-2,3-dihydroxypropane are useful in preparing β-adrenergic blocking agents.

2 Claims, No Drawings

PYROGLUTAMIC ACID SALTS OF t-BUTYLAMINO-2,3-DIHYDROXYPROPANE

CROSS REFERENCE TO RELATED APPLICATIONS

This application is a continuation of copending application Ser. No. 615,941, filed Sept. 25, 1975 now abandoned which, in turn, is, a continuation-in-part of copending application Ser. No. 532,547, filed Dec. 13, 1974, now abandoned.

BACKGROUND OF THE INVENTION

The present invention involves a novel process for resolving mixtures of enantiomers of 1-t-butylamino-2,3-dihydroxypropane from solution using a pyroglutamic acid or a tartaric acid as the resolving agent.

The sinister (S) enantiomer of 1-t-butylamino-2,3-dihydroxypropane is especially useful in preparing the more active S-isomer of the 3-substituted-4-(3-t-butylamino-2-hydroxypropoxy)-2,3,5-thiadiazole class of β-adrenergic blocking agents. These β- blocking agents and methods for their preparation are disclosed in U.S. Pat. No. 3,657,237 and U.S. Pat. No. 3,781,284. A method for preparing the S-enantiomer of 1-t-butylamino-2,3-dihydroxypropane, as disclosed in U.S. Pat. No. 3,657,237, is by the reductive alkylation of a single enantiomer reactant namely D-glyceraldehyde or isopropylidene-D-glyceraldehyde. While this method can be suitably used, it requires the use of large quantities of zinc chloride and lead tetraacetate. This results in waste streams containing large amounts of zinc and lead cations, which are objectionable from an ecological standpoint. Removal of these cations from waste streams is very difficult and expensive.

An improved process for obtaining the enantiomers of 1-t-butylamino-2,3-dihydroxypropane has been discovered. This process involves resolution of mixtures of enantiomers of 1-t-butylamino-2,3-dihydroxypropane from solution using a pyroglutamic acid or a tartaric acid as resolving agent. The process does not result in any waste stream creating ecological problems.

SUMMARY OF THE INVENTION

Process for resolving mixtures of enantiomers of 1-t-butylamino-2,3-dihydroxypropane which comprises treating said mixture in solution with a pyroglutamic acid or a tartaric acid and recovering the novel diastereoisomer which separates. The single enantiomer is then recovered from the diastereoisomer by conventional techniques.

DESCRIPTION OF THE PREFERRED EMBODIMENTS

A preferred embodiment of the present invention is a process for resolving mixtures of enantiomers of 1-t-butylamino-2,3-dihydroxypropane which comprises treating a solution of said mixture in a suitable solvent with an agent selected from S-pyroglutamic acid, R-pyroglutamic acid, L-(+)-tartaric acid and D-(−)-tartaric acid, separating, from the solution, solid diastereoisomer which forms and recovering from said diastereoisomer a single enantiomer of 1-t-butylamino-2,3-dihydroxypropane.

The symbols S and R designate the sinister (S) and rectus (R) isomer configurations of enantiomers. These designations refer to absolute spatial configurations in the molecule. The symbols L and D, (−) and (+), l and d may also be used to identify the different optical isomers. Combinations of the various symbols and designations may also be used to identify optically active isomers.

The resolving agents which are used in the present process are S-pyroglutamic acid, R-pyroglutamic acid, D (−)- tartaric acid and L (+)-tartaric acid. The resolution is carried out in solution.

Useful organic solvents include di-$C_1$-$C_3$-alkylketones such as methylethylketone, diisobutylketone, methylisobutylketone and the like, $C_3$-$C_5$ alkanols such as amylalcohol, isobutanol and the like and $C_1$-$C_4$ alkyl esters of $C_2$-$C_4$ mono-alkanoic acids such as ethyl propionate, methylbutyrate, tert-butyl acetate and the like. Small amounts of water may be admixed with these organic solvents.

When S-pyroglutamic acid is used as the resolving agent, the preferred solvents are acetone, isopropanol or mixtures of acetone or isopropanol with water. The solid diastereoisomer which separates from this resolving agent/solvent system contains the S-isomer form of the 1-t-butylamino-2,3-dihydroxypropane as S-pyroglutamic acid . S-1-t-butylamino-2,3-dihydroxypropane. When R-pyroglutamic acid is the resolving agent, the diastereoisomer obtained is R-pyroglutamic acid . R-1-t-butylamino-2,3-dihydroxypropane.

When D(−)- or L (+)-tartaric acid is the resolving agent, again the preferred solvents used are acetone, isopropanol or isopropanol/water mixtures. A most preferred solvent for this system is isopropanol containing water, and preferably about 10% by weight of $H_2O$. In carrying out the resolution with the L (+)-tartaric acid, the diastereoisomer isomer which separates contains the R-form of the 1-t-butylamino-2,3-dihydroxypropane as L (+)-tartaric acid. R-1-t-butylamino-2,3-dihydroxypropane salt — with the D (−)-acid, the diastereoisomer which separates contains the S-form of the 1-t-butylamino-2,3-dihydroxypropane as D (−)-tartaric acid.S-1-t-butylamino-2,3-dihydroxypropane salt.

The resolution process may be carried out at any suitable temperature. The resolution is generally accomplished at room temperature, although higher or lower temperatures may be used. If desired, the mixture of enantiomers and the resolving agent can be refluxed to insure complete solution and proper contact of the enantiomers and resolving agent. The refluxed solution is then cooled to room temperature or lower, generally with agitation, whereupon the diastereoisomer separates.

The present process is carried out at atmospheric pressure. Super atmospheric pressure is not required.

The amount of resolving agent used may be varied. Generally, between about 0.5 to 1 mole of resolving agent is used per mole of enantiomer mixture. Molar ratios of resolving agent: enantiomer of 0.5:1 or 1:1 are particularly useful.

The single enantiomer of 1-t-butylamino-2,3-dihydroxypropane is recovered from the separated diastereoisomer by conventional techniques. For example, the S-pyroglutamic acid.S-t-butylamino-2,3-dihydroxypropane diastereoisomer can be treated with a suitable base whereby the S-1-t-butylamino-2,3-dihydroxypropane is freed from the S-pyroglutamic acid. The S-1-t-butylamino-2,3-dihydroxypropane can then be recovered by extraction with a suitable solvent and the solvent stripped to yield the desired S-1-t-butylamino-2,3-dihydroxypropane. The neutralized S-pyroglutamic acid can be conventionally recovered from the remaining solution for re-use as a resolving agent.

Another procedure for recovering the amine enantiomer from the separated diastereoisomer is to run a solution of the diastereoisomer through a suitable ion exchange resin column and then elute the free 1-t-butylamino-2,3-dihydroxypropane enantiomer.

The mixture of enantiomers which can be resolved by the present process contain S and R enantiomers of 1-t-butylamino-2,3-dihydroxypropane. These mixtures include (R,S) racemic mixtures or modifications as well as mixtures rich in R or S enantiomer.

The resolution process is relatively simple. It involves preparing a solution of the mixture of enantiomers of 1-t-butylamino-2,3-dihydroxypropane in one of the solvents described above. The concentration of the enantiomer mixture in the solution can be varied. The resolving agent is then added either directly or as a solution in one of the aforesaid solvents. After the solid diastereoisomer drops out of the solution, it is separated from the solution by any convenient means e.g. by filtration, by centrifugration. This solid diastereoisomer is then treated by conventional techniques to recover the single enantiomer of 1-t-butylamino-2,3-dihydroxypropane. The remaining solution which is rich in the diastereoisomer containing the other enantiomer form of 1-t-butylamino-2,3-dihydroxypropane can also be treated to recover this other enantiomer.

As pointed out above, the enantiomers of 1-t-butylamino-2,3-dihydroxypropane are useful in preparing β-adrenergic blocking agents, such as those described in U.S. Pat. No. 3,657,237. The S-enantiomer of 1-t-butylamino-2,3-dihydroxypropane is especially useful for preparing the more active S-isomer of the U.S. Pat. No. 3,657,237 β-adrenergic blocking agents.

Following are examples which illustrate the resolution process of the present invention.

EXAMPLE 1

A. Preparation of R,S-1-t-butylamino-2,3-dihydroxypropane

A solution of R,S-glycidol (105 g; 1.42 moles) in 100 ml of isopropanol was added dropwise over one hour to a solution of t-butylamine (197 g; 2.7 moles) in 200 ml isopropanol while maintaining the temperature between 46° – 70° C. The solution was aged at 70° C. for one hour and the excess t-butylamine was recovered by atmospheric distillation. The distillation was continued until the pot temperature reached 110° C. Acetone (700 ml) was then added to the residue and the temperature of the final solution was adjusted to 40°-45° C. The yield of R,S-t-butylamino-2,3-dihydroxypropane (R,S-glycolamine) was 88%.

B. Resolution of R,S-1-t-butylamino-2,3-dihydroxypropane

To the final solution from (A) was added 83.0 g (0.645 moles) of S-pyroglutamic acid (97% pure) and the resultant solution mixture was refluxed, with stirring, for 1.5 hours. This solution was then cooled to room temperature over 2.5 hours, with stirring.

The S-pyroglutamic acid.S-1-t-butylamino-2,3-dihydroxypropane diastereoisomer which separated from the solution was filtered off and washed with 2×50 ml of acetone. The yield of pure diastereoisomer was 130 g (33.5% based on the R,S-glycidol).

C. Regeneration of S-1-t-butylamine-2,3-dihydroxypropane

The S-1-t-butylamino-2,3-dihydroxypropane was regenerated from the (B) diastereoisomer by dissolving the diastereoisomer in 200 ml of water and passing the solution through a column of 350 ml of IR-120 (H+). IR-120 (H+) is a gelular, strongly acidic, cation exchange resin marketed by Rohn & Haas Company. The column was washed with water until a negative test for pyroglutamic acid was obtained. S-pyroglutamic acid was recovered, in excess of 95% yield, by concentrating to dryness, slurrying the residue with isopropanol and filtering off the S-pyroglutamic acid.

The S-1-t-butylamino-2,3-dihydroxypropane was eluted from the IR-120 resin by washing with 5% ammonium hydroxide solution. The eluate was concentrated to dryness and the residue recrystallized from 150 ml of xylene to give 66.0 g of pure S-1-t-butylamino-2,3-dihydroxypropane. (31.7% yield based on the weight of R,S-glycidol)

EXAMPLE 2

R,S-t-butylamino-2,3-dihydroxypropane (5.88 g) and S-pyroglutamic acid (2.70 g) were mixed in isopropanol (20 ml) and heated on a steam bath until solution was complete. The solution was cooled to 50° C and seeded with the pure S-pyroglutamic acid.S-1-t-butylamino-2,3-dihydroxypropane salt. The mixture was then allowed to cool slowly to room temperature with stirring over about a two hour period. The slurry was cooled at 0.5° C for one hour and filtered to give 4.03 g (73%) of the S-pyroglutamic acid.S-1-t-butylamino-2,3-dihydroxypropane diastereoisomer, having a melting point of 140°-143° C; $[\alpha]_D = (-)21.9°$ (CH$_3$OH). Recrystallization from 3.5 volumes of boiling isopropanol gave a 91.5% yield of the pure diastereoisomer melting at 143°-146°; $[\alpha]_D = -23.4$ (C=2 in CH$_3$OH).

Pure S-1-t-butylamino-2,3-dihydroxypropane was recovered from the pure diastereoisomer by dissolving the diastereoisomer in excess 50% aqueous NaOH solution and extracting the S-1-t-butylamino-2,3-dihydroxypropane with ether. The ether extract was dried over magnesium sulfate and filtered. The product obtained was pure S-1-t-butylamino-2,3-dihydroxypropane characterized by melting point of 83°-85° C and $[\alpha]_D = (-)30°$ (1N HCl).

Alternately, the S-1-t-butylamino-2,3-dihydroxypropane was recovered by dissolving the diastereoisomer in 10 ml of water and using the ion exchange resin (IR-120) procedure of Example 1 (C).

EXAMPLE 3

A mixture of L (+)-tartaric acid (35.0 g) and R,S-t-butylamino-2,3-dihydroxypropane (34.4 g) were dissolved in 500 ml of hot 90% isopropanol/10% water. The solution was slowly cooled to room temperature over four hours with stirring. The L (+)-tartaric acid.R-1-t-butylamino-2,3-dihydroxypropane diastereoisomer which separated was filtered. The yield was 45.6 g of the diastereoisomer having a melting point of 85° C and $[\alpha]_D = +9.5°$. Two additional recrystallizations from aqueous isopropanol gave substantially pure L (+)-tartaric acid.R-1-t-butylamino-2,3-dihydroxypropane diastereoisomer, having a melting point of 94°-96° C and $[\alpha]_D = +19.9°$, (C=2 in 1NHCl).

The pure R-1-t-butylamino-2,3-dihydroxypropane was recovered from the diastereoisomer by substantially the same procedure as described in Examples 1 and 2.

Claims to the invention follow.

What is claimed is:

1. R-pyroglutamic acid.R-1-t-butylamino-2,3-dihydroxypropane.

2. S-pyroglutamic acid.S-1-t-butylamino-2,3-dihydroxypropane.

* * * * *